United States Patent [19]

Peterman et al.

[11] Patent Number: 4,637,672
[45] Date of Patent: Jan. 20, 1987

[54] RADIOTRANSPARENT LEAD ASSEMBLY FOR MONITORING ELECTRODES

[75] Inventors: Stanley Peterman; Charles W. Orrestad; Paul Iwanczuk, all of King County, Wash.

[73] Assignee: Quinton Instrument Company, Seattle, Wash.

[21] Appl. No.: 626,374

[22] Filed: Jun. 28, 1984

[51] Int. Cl.⁴ ...................... H01R 11/24; H01R 4/02; A61B 5/04
[52] U.S. Cl. ............................. 339/61 R; 128/639; 339/275 R; 339/278 C
[58] Field of Search .............. 339/61 R, 200 P, 255 P, 339/260, 261, 275 C, 275 R, 278 D, DIG. 3; 128/639-641, 642-644

[56] References Cited

U.S. PATENT DOCUMENTS

| 2,712,048 | 6/1985 | Huetten et al. | 339/275 C X |
| 3,708,779 | 1/1973 | Enright et al. | 339/99 R |
| 4,040,697 | 8/1977 | Ramsay et al. | 339/61 R |
| 4,050,453 | 9/1977 | Castillo et al. | 128/640 |
| 4,268,101 | 5/1981 | Stone | 339/61 R |

Primary Examiner—Gil Weidenfeld
Assistant Examiner—Steven C. Bishop
Attorney, Agent, or Firm—Seed and Berry

[57] ABSTRACT

A radiotransparent lead assembly. A nonconductive clip is provided with two opposing jaws. One jaw is provided with a conductive contact elements to make electrical contact with a monitoring electrode. The clip is connected by a radiotransparent insulated conductor to a connector for electrical connection to diagnostic equipment.

12 Claims, 7 Drawing Figures

RADIOTRANSPARENT LEAD ASSEMBLY FOR MONITORING ELECTRODES

DESCRIPTION

1. Technical Field

The present invention relates to electrocardiograph (ECG) leadwire assemblies in general, and in particular, to radiotransparent ECG leadwire assemblies.

2. Background Art

Leadwire assemblies that are used in conjunction with monitoring electrodes generally have some form of metallic spring clip at one end which connects the clip onto the stud of the electrode. This type of arrangement is disadvantageous, however, in that the use of a metal clip or the use of certain types of metal as part of the leadwire significantly interferes with the image generated during an X-ray. Disposable radiotransparent leadwire assemblies are commercially available from Concept, Inc., Clearwater, Florida and sold under the trademark R-T Electrodes TM but are relatively costly.

DISCLOSURE OF INVENTION

Briefly stated, the present invention discloses a radiotransparent lead assembly for use with diagnostic equipment and monitoring electrodes which include an electrically conductive element the lead assembly consisting of a molded, non-metallic radiotransparent electrode clip, connector means for electrically connecting the lead assembly to diagnostic equipment, and a flexible radiotransparent insulated conductor which extends between an electrical contacting element on the electrode clip and the connector means for transmitting bioelectric signals between the two.

The electrode clip comprises two opposing members, each of the members having a first end and a second end, the first end of one of the members provided with an electrical contacting element for contacting with the electrically conductive element of the monitoring electrode, the members connected by an integral molded flexible bridge, the bridge cooperating with the second ends which are manually operable to separate the first ends for attachment to the stud of the monitoring electrode. Connector means, connected to one end of the conductor, include a body having slidably mateable end portions thereon.

BEST MODE FOR CARRYING OUT THE INVENTION

Figure 2:
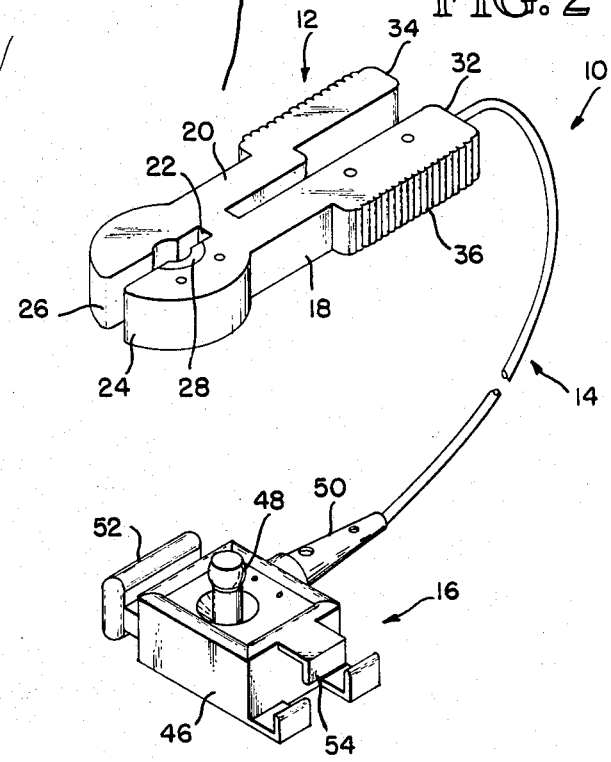
FIG. 2 is an isometric view of a lead assembly embodying the present invention.

In reference to FIG. 2, the radiotransparent lead assembly 10 therein shown consists generally of a molded, radiotransparent electrode clip 12, a flexible radiotransparent insulated conductor 14, and a connector 16. The electrode clip 12 is substantially non-metallic and is formed from two opposing arms or members 18 and 20 connected together by an integral molded flexible bridge 22.

Figure 1:
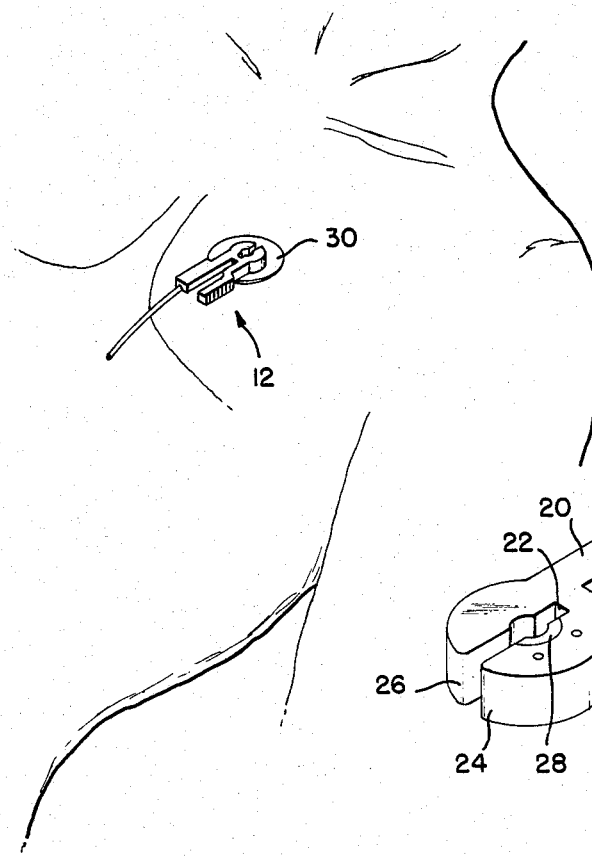
FIG. 1 is a view showing the electrode clip of the lead assembly of the present invention attached to a monitoring electrode.

The forward or first end 24 of the arm or member 18 is provided with an electrical contacting element 28 for contact with the electrically conductive element 31 of a monitoring electrode 30. As best shown in FIG. 1, the respective rearward or second ends 32 and 34 of the members 18 and 20 are adapted to be manually operable to separate the first ends 24 and 26 of the members for attachment to the monitoring electrode, the shape of the of the first ends being adapted to almost universally receive a variety of conductive elements or studs 31 projecting from the electrode. It is preferably to form the outward face of the second ends 32 and 34 with a series of ridges 36 to prevent the electrode clip from slipping out of an individual's fingers when pressure is applied thereon.

Referring again to FIG. 2, the connector 16 is generally comprised of a body 46 having an outwardly projecting electrical contacting post 48, a stem 50, and slidably mateable end portions 52 and 54. The end portions are in the form of a male end portion on one end and female end portion on the other end, the male portion adapted to be slidably received in the corresponding female portion of an adjacent connector.

As shown in FIG. 2, the insulated conductor 14 extends between the contacting element 28 held by the member 18, and the connector 16 for transmitting bioelectric signals therebetween. The insulated conductor is preferably formed with a copper wire core having a diameter of not more than 0.005 inches, but preferably not smaller than 0.001 inches to insure that it remains radiotransparent and that the resistance of the leadwire assembly does not substantially exceed 3 to 4 ohms.

Figure 3:
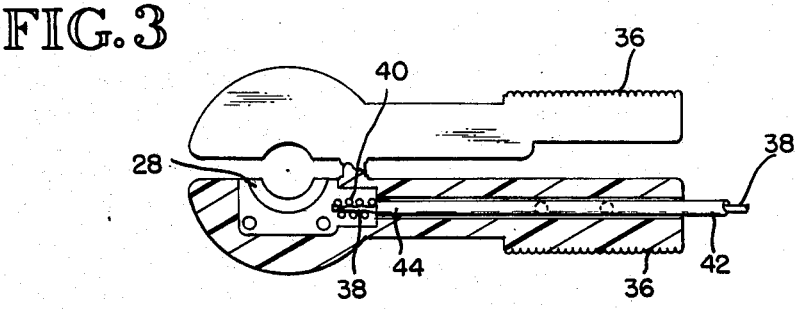
FIG. 3 is a top view of an electrode clip of the assembly of FIG. 2 with a portion thereof shown in cross-section.
Figure 4:
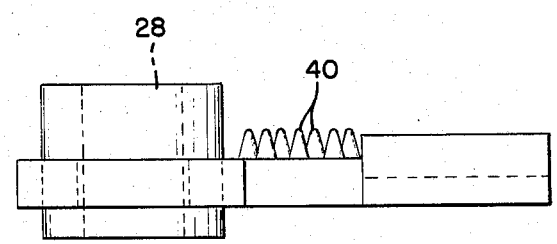
FIG. 4 is a side elevational view of the electrical contacting element of FIG. 3.

Turning now to FIG. 3, the interior of the first end 24 of the electrode clip 12 has been broken away to show the wire portion 38 of the insulated conductor 14 as it would be positioned within the member 18. The wire portion 38 is fitted between a series of plastic cones 40, best shown in FIG. 4, which project upward from the lower half of the member 18.

During the manufacturing process, the wire portion 38 and the insulating covering 42 of the conductor 14 are positioned along a trough 44 which extends forward from the rearward or second end 32 of the member 18 and terminates just short of the series of cones 40. The wire portion 38 is adapted to extend forward onto the cones 40 while the insulating covering 42 remains nested within the trough 44.

Figure 5:
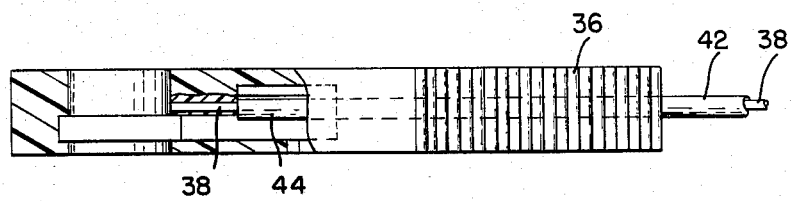
FIG. 5 is a side elevational view of the clip of FIG. 3 illustrating and showing insulated conductor mounted within the electrode clip.

Once the wire portion is positioned upon the cones 40, the combination of the wire portion and the cones is subjected to a source of heat sufficient to melt the plastic cones around the wire portion, thereby holding the wire portion in place, as best shown in FIG. 5. To complete the electrical connection necessary between the wire portion 38 and the contacting element 28, the area immediately between the wire portion and the contacting element is painted with a continuous metallic coating, preferably a silver metal coating, which acts as a conductive bridge for the transmission of a bioelectric signal received by the contacting element 28 to the wire portion of the insulated conductor 14. To facilitate the reception of this bioelectric signal from the stud on the monitoring electrode 30, the element 28 is formed in the shape of a half circle, a corresponding shape being provided immediately opposite the element 28 in the first end 26. Further, the element 28 is provided with a metallic coating, also preferably a silver metal coating, to increase the conductivity between the stud 31 and the wire portion 38. If the stud 31 on the monitoring electrode is coated with a conductive metal other than silver, it may be preferable to coat the contacting element 28 with a similar such metal in order to avoid the possibility of creating an unstable baseline, more commonly referred to as baseline drift.

Although a silver metal coating exhibits superior conductivity characteristics, one alternative to utilizing such a continuous metallic coating is utilize a conductive plastic, such as carbon fiber within plastic to transmit the bioelectric signal through the element 28 to the wire portion 38.

Once the metallic coating has been applied, the lower half of the member 18 is subsequently encased within a layer of nonconductive plastic. This layer secures the insulated conductor 14 within the trough 44 as well as forming a portion of the exterior of the member 18.

Figure 6:
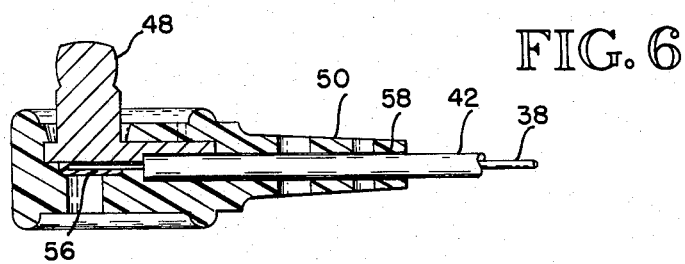
FIG. 6 is a vertical cross-sectional view of a connector of the assembly of FIG. 2.
Figure 7:
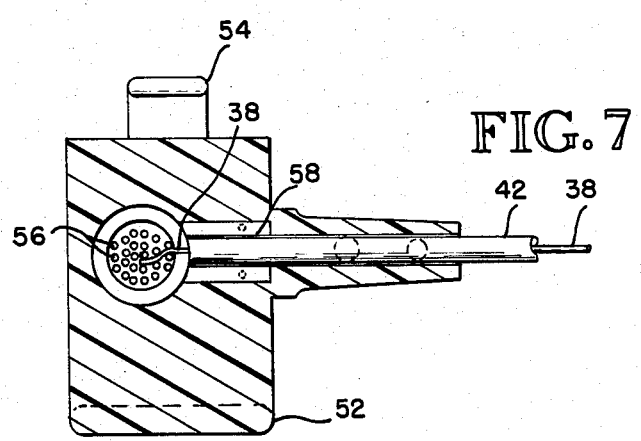
FIG. 7 is a bottom view of the connector of the assembly of FIG. 2 with the manner of connecting the leadwire shown.

Turning now to FIG. 6, the free end of the insulated conductor 14 is shown adjacent to the connector 16 before being fixed in position thereon. Similar to the method in which the wire portion is fixed to the member 18, the wire portion 38 of the free end of the insulated conductor is placed upon a series of plastic cones 56, The cones extending outward from one-half of the body 46. The insulating covering 42 extends along the wire portion 38 but terminates consistent with the end of a trough 58 which extends into the stem 50. Once the wire portion is positioned upon the cones 56, the combination of the two is subjected to a source of heat sufficient to melt the plastic cones around the wire portion, thereby holding the wire portion in place. Due to the number and arrangement of the cones 56, it is not necessary during the manufacturing process to precisely position the wire portion upon a specific area. Rather it is merely sufficient that it rest upon or between any variety of the cones 56.

To complete the electrical connection necessary between the wire portion 38 and the contacting post 48, a conductive metallic coating is applied to and extends between the post and the wire portion, thereby forming a conductive bridge for the transmission of the bioelectric signal originating at the electrode clip 12 attached to the monitoring electrode to the contacting post 48. Since the connector 16 is not required to be radiotransparent, an alternative to utilizing a conductive metallic coating would be to provide a metallic connector within the body 46 which is in contact with both the wire portion 38 and the contacting post 48.

To facilitate the transmission of this bioelectric signal from the post 48 to ECG diagnostic equipment (not shown), it is preferable to coat the exterior of the post with a conductive metallic coating, such as silver.

Once the metallic coating has been applied, the upper half of the body 46 is encased within a layer of nonconductive plastic. This layer secures the insulated conductor 14 within the trough 58 as well as forming a portion of the exterior of the body 46.

From the foregoing, it will be appreciated that, although specific embodiments of the invention have been described herein for purposes illustration, various modifications may be made without deviating from the spirit and scope of the invention. Accordingly, the invention is not limited except by the appended claims.

We claim:

1. A radiotransparent lead assembly for use with diagnostic equipment and monitoring electrodes including electrically conductive elements thereon, comprising:

a molded, substantially non-metallic radiotransparent electrode clip having two opposing members, each of said members having a first end and a second end, the first end of one of said members provided with an electrical contacting element for contacting with the electrically conductive element of the monitoring electrode, said members connected by a flexible bridge, said members extending generally perpendicular to the axis of the electrically conductive element of the monitoring electrode, said second ends being manually operable to separate said first ends for electrical attachment to the monitoring electrode;

connector means for electrically connecting the electrode clip to the diagnostic equipment; and a flexible, radiotransparent insulated conductor substantially extending between said contacting element and said connector means for transmitting bioelectric signals therebetween.

2. The lead assembly as defined in claim 1 wherein said connector means includes a body having slidably mateable end portions thereon.

3. The lead assembly as defined in claim 2 wherein said slidably mateable end portions include a male portion on one end and a corresponding female portion on the other end, the male portion adapted to be slidably received in the corresponding female portion of an adjacent connector means.

4. The lead assembly as defined in claim 2 wherein said connector means includes an electrical contacting post projecting outwardly from said body.

5. The lead assembly as defined in claim 1 wherein said electrical contacting element is electrically connected to said insulated conductor by means of a continuous metallic coating which extends between said element and said conductor.

6. The lead assembly as defined in claim 5 wherein said metallic coating is a silver metal coating.

7. The lead assembly as defined in claim 5 wherein said coating is encased within an exterior layer of nonconductive plastic.

8. The lead assembly as defined in claim 1 wherein said electrical contacting element is made of conductive plastic, said plastic transmitting a bioelectric signal to said insulated conductor.

9. The lead assembly as defined in claim 8 wherein said conductive plastic is encased within an exterior layer of nonconductive plastic.

10. A radiotransparent lead assembly for use with diagnostic equipment and monitoring electrodes having an electrically conductive element thereon, comprising:

a molded, substantially non-metallic radiotransparent electrode clip having two opposing members, each of said members having a first end and a second end, the first end of one of said members provided with an electrical contacting element for contacting with the electrically conductive element of the monitoring electrode, said members connected by an integral molded flexible bridge, said second ends being manually operable to separate said first ends for electrical attachment to the monitoring electrode;

connector means for electrically connecting the electrode clip to the diagnostic equipment, said connector means including a body having slidably mateable end portions thereon, said end portions including a male portion on one end and a corresponding female portion on the other end, said male portion adapted to be slidably received in said corresponding female portion of an adjacent connector means, said body also having an electrical contacting post projecting therefrom; and a flexible, radiotransparent insulated conductor extending between said contacting element and said connector means for transmitting bioelectric signals therebetween, said insulated conductor electrically connected to said contacting element by means of a continuous metallic coating which extends between said element and said conductor.

11. The lead assembly as defined in claim 10 wherein said metallic coating is a silver metal coating.

12. The lead assembly as defined in claim 10 wherein said coating is encased within an exterior layer of non-conductive plastic.

* * * * *